US011793983B2

(12) United States Patent
Chen et al.

(10) Patent No.: US 11,793,983 B2
(45) Date of Patent: Oct. 24, 2023

(54) SONODYNAMIC THERAPY USING MICROBUBBLES AND PULSED WAVE ULTRASOUND METHODS AND SYSTEMS

(71) Applicant: University of Pittsburgh-Of the Commonwealth System of Higher Education, Pittsburgh, PA (US)

(72) Inventors: Xucai Chen, Pittsburgh, PA (US); Qin Bin, Pittsburgh, PA (US); Villanueva Flordeliza, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 636 days.

(21) Appl. No.: 16/644,482

(22) PCT Filed: Sep. 5, 2018

(86) PCT No.: PCT/US2018/049571
§ 371 (c)(1),
(2) Date: Mar. 4, 2020

(87) PCT Pub. No.: WO2019/050963
PCT Pub. Date: Mar. 14, 2019

(65) Prior Publication Data
US 2020/0282196 A1 Sep. 10, 2020

Related U.S. Application Data

(60) Provisional application No. 62/554,469, filed on Sep. 5, 2017.

(51) Int. Cl.
*A61M 37/00* (2006.01)
*A61K 9/00* (2006.01)
*A61K 31/409* (2006.01)
*A61K 41/00* (2020.01)

(52) U.S. Cl.
CPC ....... *A61M 37/0092* (2013.01); *A61K 9/0009* (2013.01); *A61K 31/409* (2013.01); *A61K 41/0047* (2013.01); *A61M 2210/12* (2013.01)

(58) Field of Classification Search
CPC .......... A61M 37/0092; A61M 2210/12; A61K 9/0009; A61K 31/409; A61K 41/0047; A61K 41/0033; A61B 8/085; A61B 8/466; A61B 8/12
See application file for complete search history.

(56) References Cited

U.S. PATENT DOCUMENTS

| 6,498,945 | B1 | 12/2002 | Alfheim et al. |
| 9,220,718 | B2 | 12/2015 | Park et al. |
| 9,457,102 | B2 | 10/2016 | Nagishi et al. |
| 2008/0319375 | A1 | 12/2008 | Hardy et al. |
| 2009/0062724 | A1 | 3/2009 | Chen |
| 2010/0262115 | A1 | 10/2010 | Madiyalakan et al. |
| 2016/0008468 | A1 | 1/2016 | Lewis et al. |

FOREIGN PATENT DOCUMENTS

| CN | 102233159 A | 11/2011 |
| WO | WO 1999/039697 A1 | 8/1999 |
| WO | WO 2000/001413 A1 | 1/2000 |
| WO | WO 2012/143739 A1 | 10/2012 |

OTHER PUBLICATIONS

McEwan et al. "Oxygen carrying microbubbles for enhanced sonodynamic therapy of hypoxic tumours," *Journal of Controlled Release* 203: 51-56, Feb. 2015.
McEwan et al., "Polymeric microbubbles as delivery vehicles for sensitizers in sonodynamic therapy," *Langmuir* 30(49): 14926-14930, Dec. 2014.
International Search Report and Written Opinion, dated Nov. 30, 2018, issued for International Application No. PCT/US2018/049571, 8 pages.
McEwan et al., "Combined sonodynamic and antimetabolite therapy for the improved treatment of pancreatic cancer using oxygen loaded microbubbles as a delivery vehicle," *Biomaterials* 80: 20-32, Feb. 1, 2016.
Nomikou et al., "Microbubble-sonosensitiser conjugates as therapeutics in sonodynamic therapy," *Chemical Communications* 48(67): 8332-8334, 2012.
Wang et al., "Microbubbles enhance the antitumor effects of sinoporphyrin sodium mediated sonodynamic therapy both in vitro and in vivo," *International Journal of Biological Sciences* 11(12): 1401-1409, Nov. 15, 2015.

*Primary Examiner* — Robert S Cabral
(74) *Attorney, Agent, or Firm* — Klarquist Sparkman, LLP (57) ABSTRACT

The systems and methods disclosed herein relate generally to microbubble-assisted delivery of a therapeutic agent, such as a chemotherapeutic agent, to cells or tissue of interest, either in vitro or in vivo, that can be activated by directed ultrasound irradiation. For example, hydrophobic sonosensitizers can be incorporated in microbubble complexes to provide improved sonodynamic therapies.

16 Claims, 6 Drawing Sheets

SONODYNAMIC THERAPY USING MICROBUBBLES AND PULSED WAVE ULTRASOUND METHODS AND SYSTEMS

CROSS REFERENCE TO RELATED APPLICATIONS

This is the U.S. National Stage of International Application No. PCT/US2018/049571, filed Sep. 5, 2018, which was published in English under PCT Article 21(2), which in turn claims the benefit of U.S. Provisional Application No. 62/554,469, filed Sep. 5, 2017. The provisional application is incorporated herein in its entirety.

ACKNOWLEDGMENT OF GOVERNMENT SUPPORT

This invention was made with government support under grant numbers R01HL077534 and R21EB019582 awarded by the National Institutes of Health. The government has certain rights in the invention.

FIELD

The present application is directed to sonodynamic therapies using microbubbles and pulsed wave ultrasound methods and systems.

BACKGROUND

Cancer is a leading cause of death worldwide. As such, improvements and new treatments of cancer are continually being sought. In addition to diagnostic imaging, ultrasound (US) energy can be used in combination with microbubbles to provide targeted delivery of therapeutic agents, including chemotherapeutic agents. Conventional ultrasound-targeted chemotherapeutic drug delivery systems, however, have significant shortcomings and improvements to existing methods are needed.

SUMMARY

The systems and methods disclosed herein relate generally to microbubble-assisted delivery of a therapeutic agent, such as a chemotherapeutic agent, to cells or tissue of interest, either in vitro or in vivo. The therapeutic agent is activated by directed ultrasound irradiation.

In some embodiments, the systems and methods disclosed herein include incorporating hydrophobic sonosensitizers in microbubble complexes. In some embodiments, the sonosensitizers can be incorporated onto a surface of the microbubble, or otherwise encapsulated by the microbubble. In some embodiments, the sonosensitizer can be loaded into a hydrocarbon tail region of a lipid monolayer of the microbubble.

In some embodiments, US energy is delivered with a single element US transducer. In some embodiments, US energy is delivered with an array US transducer that can steer the US beam in two dimensions. In some embodiments, US energy is delivered with an array US transducer that can steer the US beam in three dimensions. In some embodiments, a mechanical scanner is used to move the US transducer to increase the treatment volume for large tumors.

In some embodiments, US wave is configured to have short pulses such as 5-10 micro-second duration but repeated at high pulse repetition rates. In some embodiments, US wave is configured to have longer pulses such as longer than 10 micro-seconds in duration but repeated at lower pulse repetition rates. In some embodiments, US wave is turned off periodically for some time such as 1-2 seconds to allow reperfusion of microbubbles to the target site.

The foregoing and other objects, features, and advantages of the invention will become more apparent from the following detailed description, which proceeds with reference to the accompanying figures. In the following description, protoporphyrin IX (PpIX) is used as an example to demonstrate the design and test procedures.

DETAILED DESCRIPTION

Definitions

As used in this application and in the claims, the singular forms "a," "an," and "the" include the plural forms unless the context clearly dictates otherwise. Additionally, the term "includes" means "comprises."

A "microbubble" as used herein refers to a microsphere comprising a shell with an approximately spherical shape surrounding an internal void comprising a gas.

The term "administered" or "administering" as used herein, refers to any method of providing a composition to a patient such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration, oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The term "target tissue" as used herein, refers to any cellular structure having biological functionality including, but not limited to, endocytosis and/or extracellular ligand binding sites that may facilitate interaction with a microbubble. A target tissue may comprise a biological cell that may be naturally occurring or synthetic and is preferably viable. Such biological cells may be a stem cell including, but not limited to, bone marrow-derived stem cells, embryonic stem cells, adult stem cells, hemopoietic stem cells, mesenchymal stem cells, epidermal stem cells, endothelial stem cells, endothelial progenitor cells, resident cardiac stem cells, pluripotent stem cells, adipose-derived stem cells, cancer stem cells (i.e., for example, a leukemic hemopoietic stem cell) or skeletal myoblasts. Alternatively, biological cells may include, but are not limited to, brain cells, liver cells, muscle cells, nerve cells, chondrocytes, lymphocytes, intestinal cells, pancreatic cells, liver cells, heart cells, lung cells, colon cells, bladder cells, uterine cells, prostate cells, urethra cells, testicular cells, and/or epithelial cells. Further, a biological cell may be a cancerous cell, for example, a dendritic cell.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed methods and apparatuses can be used in combination with other methods and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Sonodynamic therapy is an alternative cancer therapy using ultrasound to active the cytotoxicity of drugs, so called "sonosensitizers." The cytotoxic mechanism of sonodynamic therapy involves generation of reactive oxygen species (ROS) by stimulation of sonosensitizer with ultrasound and subsequent induction of cell apoptosis/death by ROS. A similar approach is photodynamic therapy, in which light, instead of ultrasound, is utilized as stimulus to activate drugs, so called photosensitizer, to exert cytotoxicity effect.

While the application of photodynamic therapy is restricted in treatment of superficial lesions due to poor penetration of light through tissues, sonodynamic therapy offer promise in treating more deeply-located and less anatomically less accessible lesions because ultrasound is capable of penetrating soft tissue up to several tens of centimeters depending on the frequency used.

Microbubble (MB)-based ultrasound contrast agents can be used in various clinical settings. There are several potential benefits of attaching sonosensitizer to MBs. First, it allows targeted site-specific delivery of the sonosensitizers by directed US stimulation at the desired treatment location. Second, the close proximity of the sonosensitizer to the MB surface may enhance the possibility of ROS generation duration microbubble cavitation or may even enhance cell entry of the sonosensitizer due to sonoporation. Third, the possibility of visualizing these drug carriers with a bubble specific imaging modality allows a theranostic approach. Because of this, various attempts have been made to conjugate sonosensitizers onto the microbubble surface. Many of the sonosensitizers are hydrophobic compounds with poor water solubility, such as hematoporphyrin and protoporphyrin IX (PpIX). It has been previously shown that sonodynamic treatment with PpIX can induce apoptosis. Poor aqueous solubility can result in delivery problems in clinical applications.

Novel systems and methods are disclosed herein of an MB formulation and preparation method to load PpIX onto MBs. We tested ROS generation of this formulation after treatment with various ultrasound conditions. We also tested its ultrasound-dependent sonodynamic effect (cell killing) and its tumor inhibition capability in a murine model of squamous cell carcinoma (SCC-VII).

Microbubble Preparation

Figure 1:
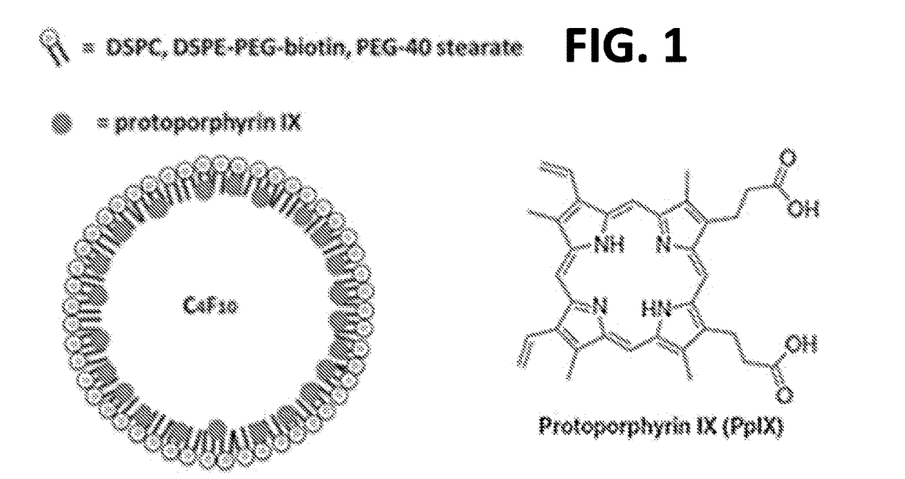
FIG. 1 illustrates a schematic diagram of a lipid microbubble encapsulating PpIX.

A schematic diagram of a lipid microbubble encapsulating PpIX is shown in FIG. 1. The PpIX is expected to be loaded in the hydrocarbon tail region of lipid monolayer due to the hydrophobic nature of this compound. For this study, perfluorobutane (C4F10) was used.

The preparation of drug loaded MB can include: (1) preparation of sonosensitizer loaded liposomes using thin-film method, the liposomes being made from a mixture of 1,2-distearoyl-sn-glycero-3-phosphocholine (DSPC), 1,2-distearoyl-sn-glycero-3-phosphoethanolamine-N-[biotin-(polyethylene glycol)-2000] (DSPE-PEG2000), and PpIX; (2) aliquot liposome in sealed vials with perfluorocarbon (PFC) gas filled in head space; (3) vigorous physical agitation of liposomes using an amalgamator in the presence of polyoxyethylene (40) stearate (ST-PEG40) and PFC.

Since the stability of liposomes can be better than microbubbles under identical storage conditions, liposomes loaded with PpIX can be stored with perfluorocarbon gas in head space as MB precursor and converted to MBs by physical agitation before use. The formulation is optimized over several formulation parameters, including concentration of surfactant (ST-PEG40), gas type (oxygen and PFC), and ratio of lipid to drug, in order to achieve stable MBs with high drug loading capacity. MBs with PpIX in the encapsulating lipid shell are henceforth designated as $MB_{PpIX}$. For control purposes, MBs without PpIX were fabricated ($MB_{Blank}$). MB size was measured with a Coulter Counter (Multisizer-III, Beckman Coulter). Stability of $MB_{PpIX}$ was measured over 7 days after activation.

Quantification of PpIX Loading Capacity on $MB_{PpIX}$

To quantify the amount PpIX loaded on the bubble surface, $MB_{PpIX}$ was dissolved in ethanol, and fluorescence of the solution (Ex: 402 nm; Em: 633 nm) was measured using DTX-880 Multimode Detector (Beckman Coulter, Brea, Calif.). The PpIX concentration was calculated based on a calibration curve that was generated by series dilution of PpIX stock solution of known concentrations.

ROS Generation of $MB_{PpIX}$

The ROS generation in PpIX microbubble suspension and free PpIX solution (first dissolved in DMSO; final PpIX concentration: 2.9 µM), after treatment with various ultrasound (1 MHz, 10% duty cycle) intensities for 2 min, was measured using Amplex Red assay.

Cytotoxicity of $MB_{PpIX}$ In Vitro

Mouse squamous cell carcinoma cells SCC-VII were cultured in RPMI 1640 medium supplemented with 10% fetal bovine serum (FBS), 200 mg/mL streptomycin and 200 IU/mL penicillin (Gibco, ThermoFisher Scientific, Waltham, Mass.). Cells were harvested and suspended in a concentration of $1 \times 10^6$ cells/mL using serum free RPMI-1640 medium. Every 2 mL of cell suspension was transferred to 14 mL Falcon round-bottom polystyrene tubes. Immediately before the US treatment, the suspension was supplemented together with various concentrations of $MB_{PpIX}$. US (1 MHz, 10% duty cycle) exposure time for each acoustic condition is 2 min. During exposure, the sample tube was gently shaking occasionally (every 10 sec) to improve mixing and to provide uniform exposure. Free PpIX (first dissolved in DMSO; final concentration: 2.9 µM) or PpIX liposome (precursor of $MB_{PpIX}$, with equivalent PpIX concentration of 2.9 µM) were used for comparison and cells not treated were used as controls (NT). After treatment procedure, 300 µL of the cell suspension was transferred to a 24 well plate prefilled with 2 mL cell culture medium, and the cells were incubated at 37° C. for 24 hours. Cell viability was then measured using alamarBlue cell viability assay. Cell morphology was examined with bright field microscopy (IX81, Olympus, Center Valley, Pa.).

In Vivo Tumor Inhibition of $MB_{PpIX}$ with US

The animal experimental protocols were approved by the Institutional Animal Car and Use Committee (IACUC) at the University of Pittsburgh and adhered to the guidelines for Humane Use of Animals in Laboratory Research. For in vivo test of cytotoxicity and tumor inhibition, an orthotopic model of mouse squamous cell carcinoma was used. C3H/NeJ female mice were administered $1.5 \times 10^6$ SCC-VII cells subcutaneously.

Tumor Inhibition with Intratumoral Injection $MB_{PpIX}$

In order to accommodate intratumoral injection of $MB_{PpIX}$, the tumor was allowed to grow to 165±62 µL (6-7 days after tumor inoculation). On Day 0, SCC-VII tumor-bearing mice were randomly assigned and received intratumoral injection of $1 \times 10^8$ $MB_{PpIX}$ in 50 µL saline, equivalent dose (18.4 µg) of PpIX solution only, or $1 \times 10^8$ $MB_{Blank}$ (no PpIX), followed by 4 min of US treatment (1 MHz, $I_{SAPA}=3$ W/cm², 10 µs pulse duration with a 100 µs pulse interval resulting in 10% duty cycle). The treatment was repeated up to 3 times at Days 0, 3 and 6. To insurance identical dose of PpIX in the MB formation and the PpIX solution, the PpIX solution was generated by crushing the $MB_{PpIX}$ in an identical amount of MB suspension with over pressurization. Tumor volume was serially imaged with three dimensional (3D) high resolution ultrasound every 3 days. Each animal was sacrificed once the tumor volume exceeded 1000 µL according approved protocol.

Tumor Inhibition with Intravenous Infusion of $MB_{PpIX}$

In another group of animals, an indwelling catheter was surgically placed in the internal jugular vein for intravenous infusion of MB, 4 days after tumor inoculation and 2 days prior to the first treatment. On Day 0, SCC-VII tumor-bearing mice were randomly assigned and received intravenous infusion of $2 \times 10^8$ $MB_{PpIX}$ in 100 uL of saline, equivalent dose (36.8 µg) of PpIX only, or same dose of $MB_{Blank}$ (no PpIX,), through the internal jugular vein over 3 min, during US treatment (1 MHz, $I_{SPPA}=3$ W/cm², 10% duty cycle). US treatment continued for another min after the infusion for a total of 4 min treatment duration. The treatment was repeated again at Day 3. Same as for the intratumoral injection Group, the PpIX solution was generated by crushing the MBs in an identical amount of $MB_{PpIX}$ suspension with over pressurization to insurance identical dose of PpIX in the MB formation and the PpIX solution. Tumor volume was serially imaged with 3D high resolution US every 3 days. Each animal was sacrificed once the tumor volume exceeded 1000 µL according approved protocol.

Serial Ultrasonic Measurements of Tumor Volume

High resolution 3D ultrasound imaging was used to quantify tumor volume at 3-day intervals. Cross-sectional images of the tumor were acquired at 0.2-mm step size using an automated mechanical scanning system with a 30 MHz transducer for small tumor (<250 µL) or 21 MHz transducer for larger tumor (Vevo 2100, VisualSonics, Toronto, Canada). Tumor outlines were manually drawn in representative images and volumes were computed from reconstructions of the tumor outlines in 3D.

Tumor volume was then fitted to the exponential growth function as $V=V_0\exp(kt)$ where $V_0$ was the initial tumor volume at Day 0 and k was the growth rate. A two-parameter least-squared-error fit was performed on all available data points for each animal. Tumor doubling time was calculated as $DT=\ln(2)/k$. For group comparison, the tumor volume was normalized by its initial value at Day 0.

Ultrasound Imaging of Tumor Tissue During Therapy

During MB infusion and therapeutic US delivery, the tumor tissue was imaged periodically using Contrast Pulse Sequence (CPS), a contrast-specific modality (Acuson Sequoia, Siemens, Mountain View, Calif.). Low mechanical index (MI=0.2) time-triggered (time interval 0.2 s) imaging at 7 MHz transmit frequency was used for this purpose.

Therapeutic Ultrasound Delivery

Pulsed wave therapeutic ultrasound was delivered with a single-element transducer driven with a function generator (33250A; Agilent, Santa Clara, Calif., USA) and power amplifier (100A250A; Amplifier Research, Souderton, Pa., USA). For in vitro ROS generation and cytotoxicity studies, US at 1 MHz center frequency was delivered with a flat disk transducer (A303S, ½ inch diameter, Olympus NDT, Waltham, Mass., USA), with various spatial average pulse average intensities ($I_{SAPA}$) and duty cycles.

For tumor inhibition study with intratumoral injection of $MB_{PpIX}$, US at 1 MHz center frequency was delivered with a flat disk transducer (A303S, ½ inch diameter, Olympus NDT) at $I_{SAPA}$=3 W/cm$^2$, with a pulse duration of 10 μs, pulse interval of 100 μs, resulting in a duty cycle of 10%. The tumor volume was placed in the nearfield of the therapeutic transducer. Spatial average temporal average intensity ($I_{SATA}$) Was 0.3 W/cm$^2$. For tumor inhibition study with intravenous infusion of $MB_{PpIX}$, US at 1 MHz center frequency was delivered with a focused disk transducer (A302S, 1 inch diameter, 1.63 inch focus, −6 dB beam diameter 3.5 mm, Olympus NDT) at a spatial peak pulse average intensity ($I_{SPPA}$) of 3 W/cm$^2$, with a pulse duration of 10 μs, pulse interval of 25 μs, with the pulse train on for 0.5 s every 2 s to allow reperfusion of MB to the treatment area. The overall duty cycle was 10%. The tumor volume was placed in the focal area of the transducer. The spatial peak temporal average intensity ($I_{SPTA}$) was 0.3 W/cm$^2$. $I_{SATA}$ over the tumor area was variable depending on the tumor size but less than 0.3 W/cm$^2$. A custom cone-shaped US waveguide was used to couple the US wave to the tumor site. This arrangement was used to reduce possible undesirable US toxicity to other organs such as the intestine when MB was infused. The US transducers and the delivery system were calibrated with a 200-μm capsule hydrophone (HGL-0200, Onda Corp, Sunnyvale, Calif.) in free space.

Data were expressed as the mean±standard deviation (SD). The difference between two groups was determined by Student's t-test (two-tailed), with p<0.05 being considered statistically significant. Statistical comparisons among more than two groups were performed using one-way ANOVA, with significance defined as p<0.05. If ANOVA demonstrate a significant difference among the groups, post-hoc Tukey's test was performed to examine whether the difference between two groups is statistically significant.

Properties of PpIX Loaded MB

Figure 2A:
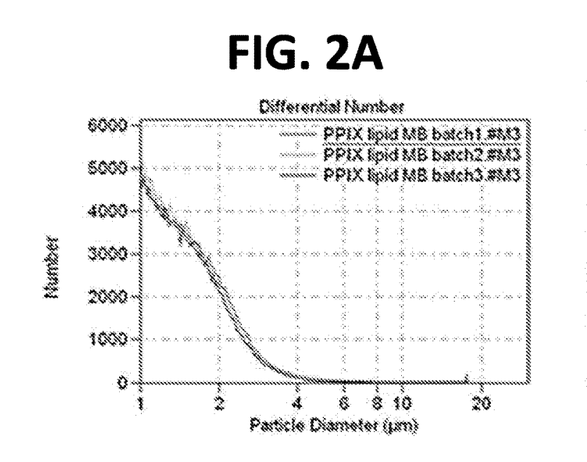
FIG. 2A illustrates a size distribution of 3 representative lots of PpIX loaded MB.
Figure 2B:
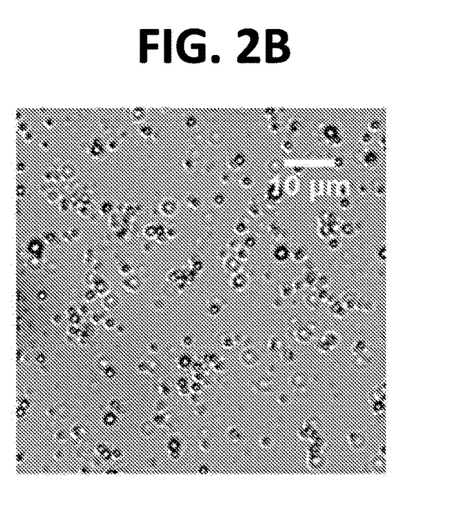
FIG. 2B shows a Bright field microscopic image of PpIX loaded MB.

A stable formulation of PpIX-loaded MBs was achieved with high drug loading capacity. Several critical formulation parameters were adjusted, including concentration of surfactant (ST-PEG40), gas type, and ratio of lipid to drug, in order to achieve stable MBs with high drug loading capacity. The size distribution from three representative lots of PpIX loaded MBs is shown in FIG. 2A. FIG. 2B illustrates a Bright field microscopic image of PpIX loaded MB The mean size of the MB was 1.6±0.1 μm, with a typical concentration of 5.5×10$^9$ MB/mL. The PpIX loading capacity was 184±49 μg per 10$^9$ MB, or equivalent concentration of PpIX of 1.01 μg/mL with a typical formation.

Figure 3A:
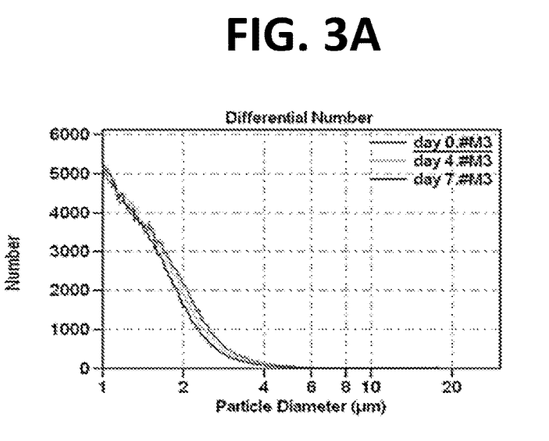
FIG. 3A shows a size distribution of a batch of $MB_{PpIX}$, measured at day 0, 4 and 7 after activation, demonstrating its stability.
Figure 3B:
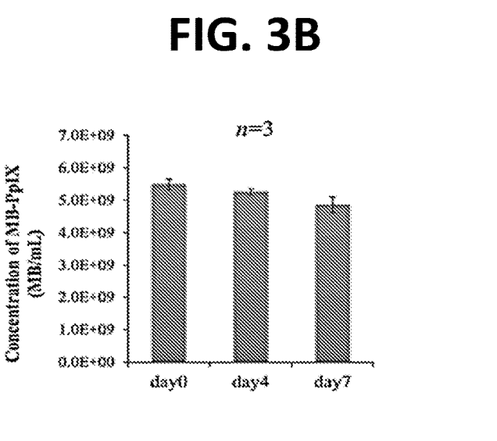
FIG. 3B shows a summary of stability of 3 batches of $MB_{PpIX}$.

When stored at 4° C., the activated MB remained stable for at least 7 days, as measured with the Coulter Counter (FIG. 3). FIG. 3A illustrates a size distribution of the same batch of MBPpIX, measured at day 0, 4 and 7 after activation. FIG. 3B illustrates a summary of stability of 3 batches of MB-PpIX. No significant MB concentration or size change was detected over 7 days (n=3).

Since the stability of liposomes is often much better than microbubbles under identical storage condition, liposomes loaded with PpIX can be stored with perfluorocarbon gas in head space as MB precursor and converted to MBs by physical agitation before use.

ROS Generation Capability of $MB_{PpIX}$

The ROS generation in MBPpIX suspension and PpIX solution (PpIX concentration: 2.9 μM), after treatment with various ultrasound intensities for 2 min, has been measured using Amplex Red assay.

Figure 4:
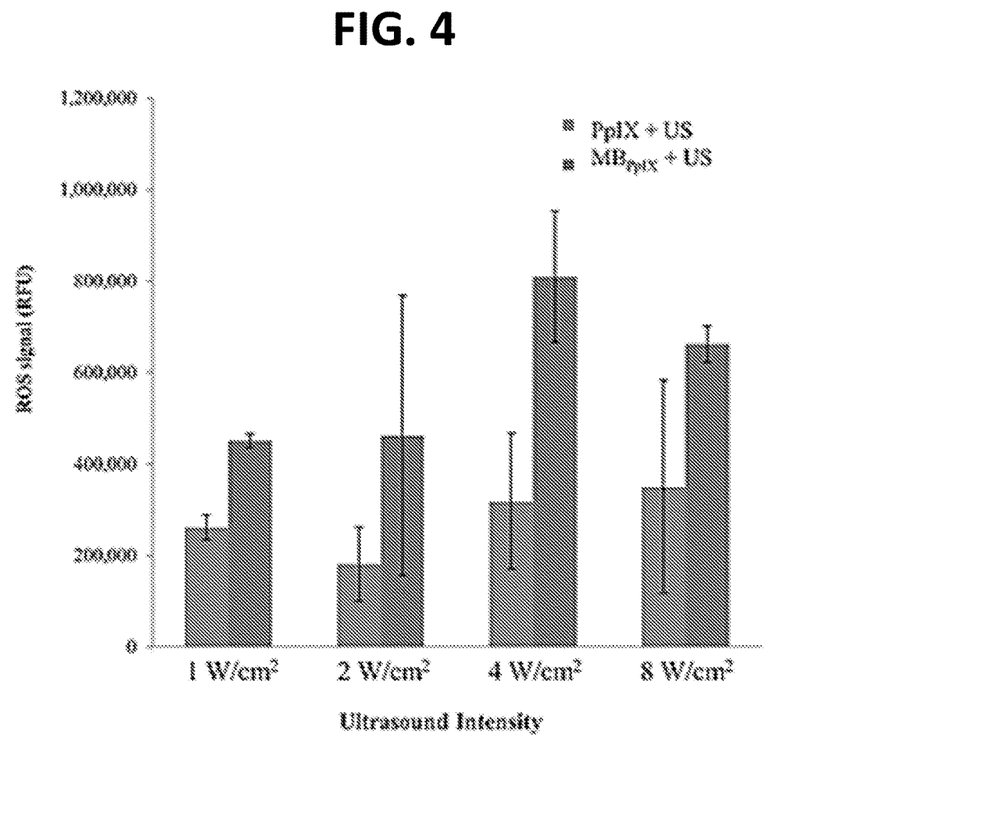
FIG. 4 shows the capability of reactive oxygen species (ROS) generation in $MB_{PpIX}$ suspension and PpIX solution (PpIX concentration: 2.9 µM), after treatment with various ultrasound intensities for 2 min, as measured using Amplex Red assay (n=2). ROS generation was detected in both PpIX solution and $MB_{PpIX}$ suspension. There were more generated ROS in $MB_{PpIX}$+US group than PpIX+US group in identical ultrasound conditions.

FIG. 4 illustrates the ROS generation in $MB_{PpIX}$ suspension and PpIX solution (PpIX concentration: 2.9 μM), after treatment with various ultrasound intensities for 2 min, as measured using Amplex Red assay (n=2). ROS generation was detected in both PpIX solution and PpIX MBs suspension, in an ultrasound intensity dependent manner. Broadly, there were more generated ROS in MBPpIX+US group than PpIX+US group in identical ultrasound conditions.

Cytotoxicity of $MB_{PpIX}$ In Vitro

Figure 5:
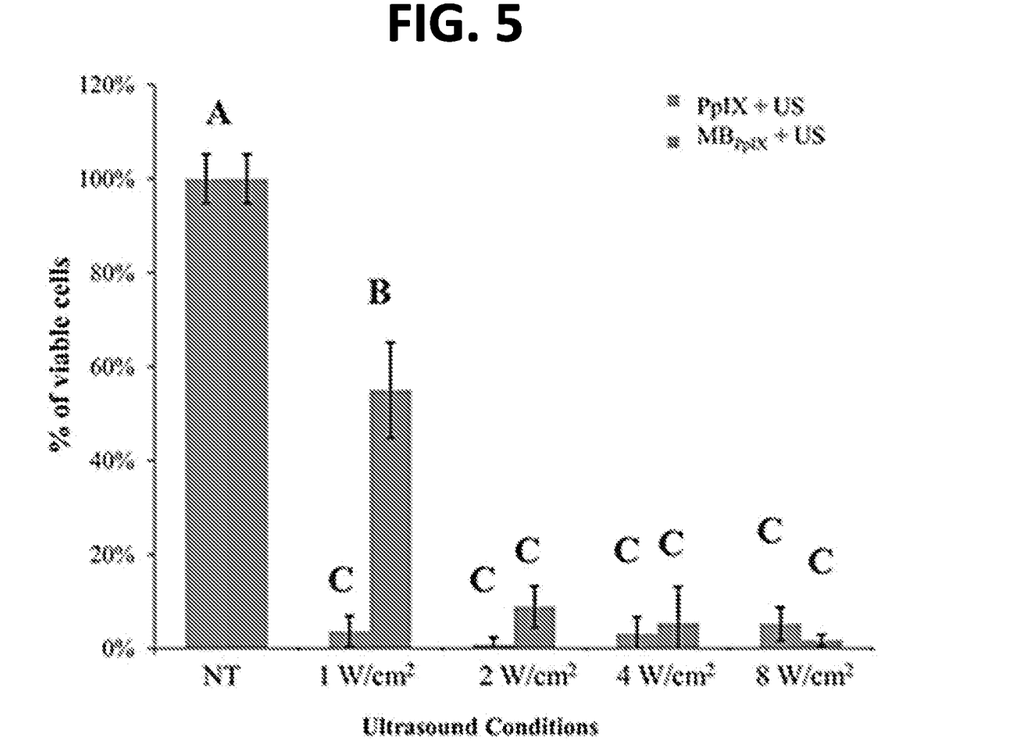
FIG. 5 shows a cytotoxicity effect of PpIX or $MB_{PpIX}$ treated with ultrasound (n=3 for each conditions) at various $I_{SAPA}$ and 10% duty cycle.

FIG. 5 illustrates the cytotoxicity effect of PpIX or $MB_{PpIX}$ treated with ultrasound (n=3 for each conditions) at various $I_{SAPA}$ and 10% duty cycle. Significant cell killing was overserved at all US conditions compared with NT (p<0.01). At $I_{SAPA}$ and=1 W/cm$^2$, more cell killing was observed with PpIX+US than $MB_{PpIX}$+US (cell viability 4±3% vs 55±10%, p=0.01). A possible explanation for this difference is that in the PpIX solution, free PpIX can diffuse into cells and there is possible ROS generation inside the cell membrane upon ultrasound irritation; in the case of $MB_{PpIX}$+US, PpIX was released only upon ultrasound mediated MB destruction, and thus, ROS is likely to occur outside the cells. At higher US intensities, no significant differences in cytotoxicity could be detected. Groups with different lettering are significantly different from each other, p<0.05).

Figure 6A:
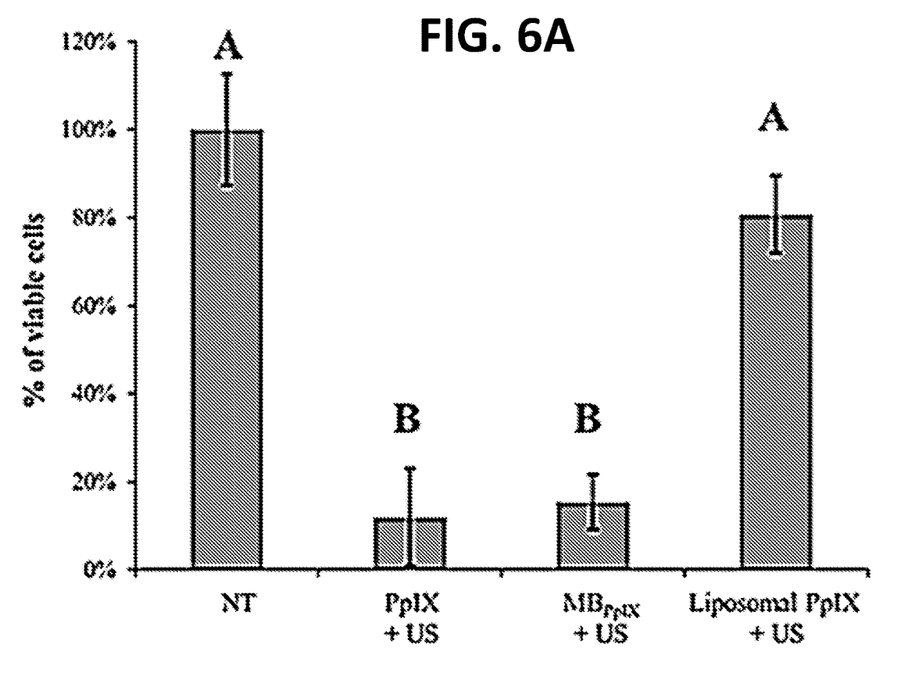
FIG. 6A shows a cytotoxicity effect of $MB_{PpIX}$ with ultrasound at fixed $I_{SAPA}$=2 W/cm$^2$ and 10% duty cycle for 2 min, with a comparison of cell viability (n=3 for each condition).
Figure 6B:
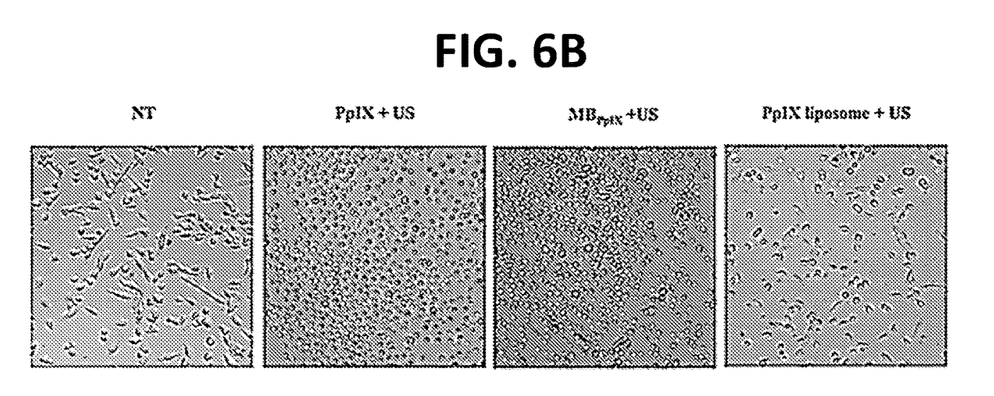
FIG. 6B shows microscopic images of the treated cells 24 hours after treatment.

The cytotoxicity effect at a fixed equivalent dose of PpIX (2.9 μM) and fixed US treatment ($I_{SAPA}$=2 w/cm$^2$, 10% duty cycle, 2 min duration) is compared in FIG. 6A, which shows cell viability (n=3 for each condition). At this US setting, both $MB_{PpIX}$ and PpIX solution achieved high levels of cell killing compared with NT control. It is worth noting that the liposomal form of PpIX, the precursor of $MB_{PpIX}$, did not induce similar cell killing effect as PpIX and $MB_{PpIX}$ after ultrasound treatment. Microscopic images 24 hr post treatment indicated that cells in both $MB_{PpIX}$+US and PpIX+US groups had cell rounding and apoptotic body, as shown in FIG. 6B (165±62 μL).

Tumor Inhibition In Vivo with Intratumoral Injection

Figure 7:
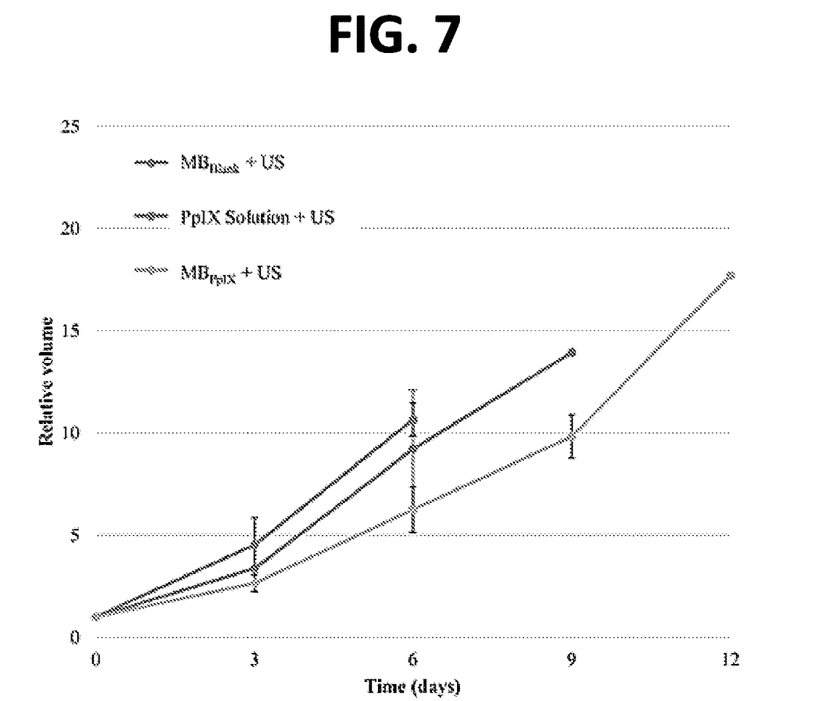
FIG. 7 shows group averages of normalized tumor volume over time with intratumoral injection.

Intratumoral injection was performed as the route of MB administration to eliminate the possible complications of pharmacokinetic behavior of the PpIX loaded MB. This allowed the successful local injection of 50 μL of $MB_{PpIX}$ or PpIX solution. Group averages of normalized tumor volume over time are shown in FIG. 7. Normalized tumor volume was significantly smaller for $MB_{PpIX}$+US than that for $MB_{Blank}$+US at day 3 and at day 6; Normalized tumor volume was significantly smaller for $MB_{PpIX}$+US than that for PpIX solution+US at day 6. Normalized tumor volume was numerically but not significantly smaller for PpIX solution+US than that for $MB_{Blank}$+US at day 3 and Day 6.

Figure 8:
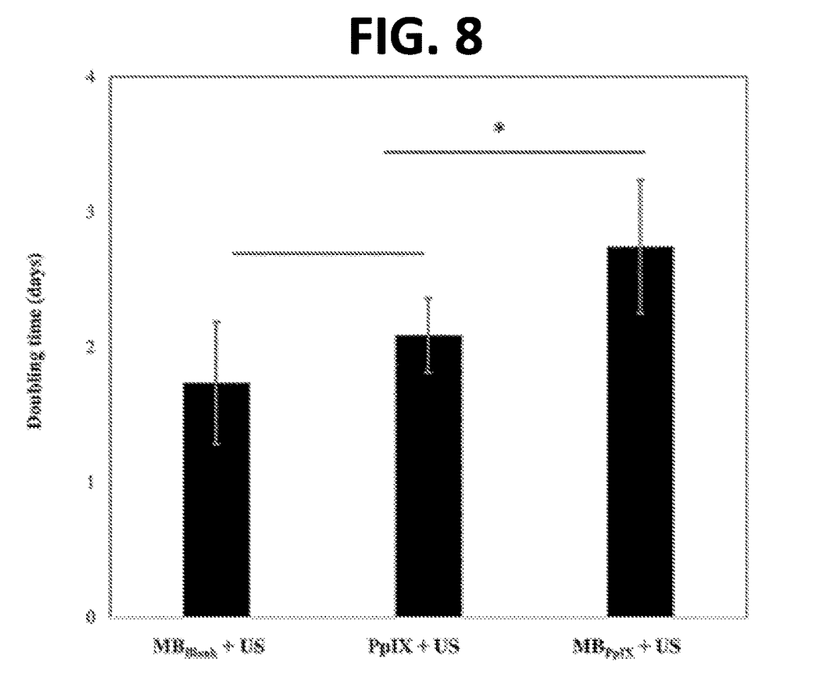
FIG. 8 provides a comparison showing that, with intratumoral injection, tumor doubling time was significantly higher for $MB_{PpIX}$+US than that for PpIX+US and significantly higher than that for $MB_{Blank}$+US.

As shown in FIG. 8, tumor doubling time was significantly higher with intratumoral injection for $MB_{PpIX}$+US than that for PpIX solution+US and significantly higher than that for $MB_{Blank}$+US; Tumor doubling time was numerically but not significantly higher for PpIX solution+US than that for $MB_{Blank}$+US.

Tumor Inhibition In Vivo with Intravenous Injection

Figure 9:
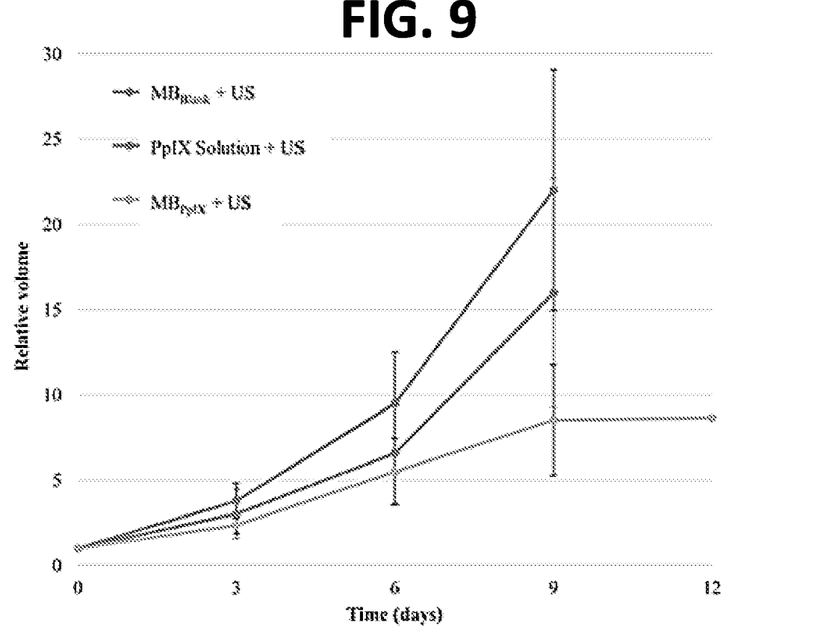
FIG. 9 shows group averages of normalized tumor volume over time with intravenous infusion.

The platform was further tested using intravenous injection of MB. The mean size of the tumor at Day 0 was 115±34 μL. Group averages of normalized tumor volume over time are shown in FIG. 9. Normalized tumor volume was significantly smaller for $MB_{PpIX}$+US than that for MBBlank+US at day 3 and at day 6; Normalized tumor volume was significantly smaller for $MB_{PpIX}$+US than that for PpIX+US at day 6.

Figure 10:
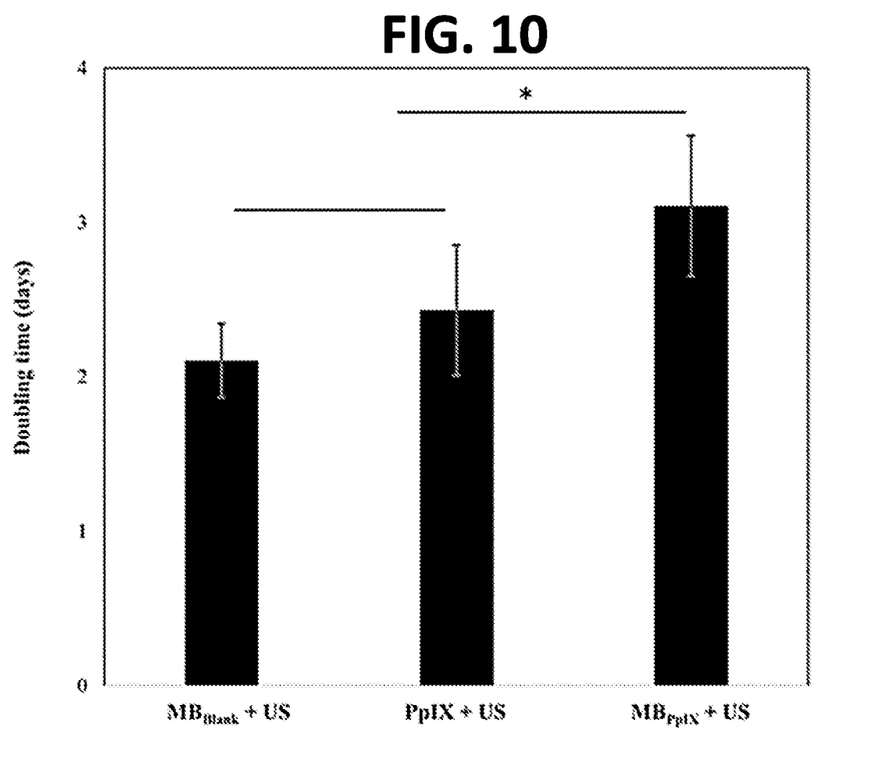
FIG. 10 provides a comparison showing that, with intravenous infusion, tumor doubling time was significantly higher for $MB_{PpIX}$+US than that for $MB_{Blank}$+US and significantly higher than that for PpIX solution+US.

As shown in FIG. 10, tumor doubling time was significantly higher for with intravenous infusion of $MB_{PpIX}$+US than that for MBBlank+US and significantly higher than that for PpIX+US; Tumor doubling time was numerically but not significantly higher for PpIX+US than that for $MB_{Blank}$+US.

Ultrasound Imaging of Tumor Tissue During Therapy

Low pressure contrast specific US imaging confirmed that MB were destroyed by the therapy pulses during the 0.5 s of pulse ultrasound with the current pulse configuration, and MB were able to reperfusion to the treatment area during US off time.

The methods and systems discussed above demonstrate a stable $MB_{PpIX}$-formulation that was achieved with high drug loading and this agent together with pulsed US can generate ROS, induce tumor cell apoptosis, and inhibit tumor growth.

As indicated by the results discussed above, sonodynamic therapy with microbubbles is a powerful approach. The MB formulation and methods described herein load PpIX onto the MBs provide significant advantages. It should be noted that this formulation and method can also be applied to other hydrophobic sonosensitizers. We have tested ROS generation in PpIX microbubble suspension after treatment with various ultrasound intensities using Amplex Red assay, and demonstrated ultrasound-dependent sonodynamic effect (cell killing) with MBPpIX+US and its tumor inhibition capability in a murine model of squamous cell carcinoma.

In conjunction with pulsed US, $MB_{PpIX}$ is an effective sonodynamic therapy platform. Thus, systems can be provided to achieve non-invasive sonodynamic therapy using systemic delivery of PpIX, whereby PpIX-carrying lipid MBs allow circulation of this otherwise insoluble compound, while also focusing and augmenting US energy for enhanced sonodynamic effect.

Various advantages and improvements can be achieved by incorporating hydrophobic sonosensitizers into microbubbles as disclosed herein.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of sonodynamic treatment of a patient, comprising:
    delivering an effective amount of a plurality of microbubble complexes to a target area of the patient; and
    subjecting the target area to ultrasound irradiation,
    wherein the plurality of microbubble complexes comprise a hydrophobic sonosensitizer in an amount of 135 μg per $10^9$ microbubbles to 233 μg per $10^9$ microbubbles.

2. The method of claim 1, wherein the sonosensitizer is incorporated onto a surface of the microbubble.

3. The method of claim 1, wherein the sonosensitizer is encapsulated into the microbubble complexes.

4. The method of claim 1, wherein the sonosensitizer is loaded into a hydrocarbon tail region of a lipid monolayer of the microbubble complexes.

5. The method of claim 1, wherein the sonosensitizer comprises protoporphyrin IX.

6. The method of claim 1, wherein the target area comprises cancerous cells.

7. A method of providing cancer therapy to a patient in need thereof, comprising
    supplying gas-filled microbubbles a targeted area of a patient, the targeted area comprising cancerous cells and the microbubbles comprising at least one hydrophobic sonosensitizer, the hydrophobic sonosensitizer being provided in an amount of 135 μg per $10^9$ microbubbles to 233 μg per $10^9$ microbubbles;
    delivering ultrasound energy generated by an ultrasound probe to the targeted area, wherein the application of ultrasound causes the microbubbles to activate or rupture, which is sufficient to induce apoptosis of at least some of the cancerous cells by reactive oxygen species.

8. The method of claim 7, wherein the ultrasound probe is an external probe.

9. The method of claim 7, wherein the ultrasound probe is an intravascular ultrasound catheter.

10. The method of claim 7, where the ultrasound frequency is 0.1-10 MHz, and preferably 0.5-2 MHz, to allow proper tissue penetration and microbubble excitation.

11. The method of claim 7, where the ultrasound probe is a single element US transducer.

12. The method of claim 7, where the ultrasound probe is an array US transducer that can steer the US beam in two or three dimensions.

13. The method of claim 7, where a mechanical scanner is used to move the US transducer to increase the treatment volume for large tumors.

14. The method of claim 7, where the ultrasound probe delivers short pulses repeated at high pulse repetition rates, wherein the short pulses are of 5-10 micro-seconds in duration.

15. The method of claim 7, where the ultrasound probe delivers longer pulses repeated at lower pulse repetition rates, wherein the longer pulses are of a duration greater than 10 micro-seconds.

16. The method of claim 1, where the ultrasound energy is turned off periodically for some time to allow reperfusion of microbubbles to the target site.

* * * * *